(12) United States Patent
Mouscadet et al.

(10) Patent No.: US 12,359,262 B2
(45) Date of Patent: Jul. 15, 2025

(54) **METHOD OF DETECTING *SALMONELLA TYPHIMURIUM***

(71) Applicant: Bio-Rad Europe GmbH, Basel (CH)

(72) Inventors: Jean-Francois Mouscadet, Marnes-la-Coquette (FR); Sophie Pierre, Paris (FR)

(73) Assignee: Bio-Rad Europe GmbH, Basel (CH)

( * ) Notice: Subject to any disclaimer, the term of this patent is extended or adjusted under 35 U.S.C. 154(b) by 0 days.

(21) Appl. No.: 18/584,709

(22) Filed: Feb. 22, 2024

(65) Prior Publication Data

US 2024/0294994 A1 Sep. 5, 2024

Related U.S. Application Data

(63) Continuation of application No. 16/310,809, filed as application No. PCT/IB2017/000921 on Jun. 15, 2017, now Pat. No. 11,946,107.

(60) Provisional application No. 62/351,130, filed on Jun. 16, 2016.

(51) Int. Cl.
*C12Q 1/689* (2018.01)
*C12Q 1/686* (2018.01)

(52) U.S. Cl.
CPC .............. *C12Q 1/689* (2013.01); *C12Q 1/686* (2013.01); *C12Q 2600/166* (2013.01); *G01N 2333/255* (2013.01)

(58) Field of Classification Search
CPC .......... C12Q 1/689; C12Q 1/686; C12Q 1/68; C12Q 1/6813; C12Q 1/6851; C12Q 1/6888; C12Q 2600/166; C12N 1/205; C12N 1/20; G01N 33/56916; G01N 2333/255; Y02A 50/30
See application file for complete search history.

(56) References Cited

U.S. PATENT DOCUMENTS

| | | | |
|---|---|---|---|
| 5,030,557 A | 7/1991 | Hogan et al. | |
| 5,541,308 A | 7/1996 | Hogan et al. | |
| 6,258,569 B1 | 7/2001 | Livak et al. | |
| 6,399,364 B1 * | 6/2002 | Reeve | C12Q 1/6874 |
| | | | 435/287.1 |
| 6,814,934 B1 | 11/2004 | Higuchi | |
| 7,476,733 B2 | 1/2009 | Carvalho et al. | |
| 7,799,522 B2 | 9/2010 | Li et al. | |
| 8,268,984 B2 | 9/2012 | Tourniaire | |

FOREIGN PATENT DOCUMENTS

| | | |
|---|---|---|
| CN | 101705307 A | 5/2010 |
| CN | 102618634 A | 8/2012 |
| CN | 103293297 A | 9/2013 |
| CN | 103266179 B | 10/2014 |
| CN | 104087654 A | 10/2014 |
| CN | 104830988 A | 8/2015 |
| EP | 1911852 A1 | 4/2008 |
| WO | 9500664 A1 | 1/1995 |
| WO | WO2015/026757 A2 * | 2/2015 ............... C12Q 1/68 |
| WO | 2015148785 A1 | 10/2015 |

OTHER PUBLICATIONS

Kim, H.J., et al. "Identification of *Salmonella enterica* Serovar Typhimurium using Specific PCR Primers obtained by Comparative Genomics in Salmonella Serovars," J Food Prot., vol. 69, No. 7, Jul. 1, 2006, pp. 1653-1661.
International Search Report, dated Oct. 2, 2017, for corresponding International Patent Application PCT/IB2017/000921, 5 pages.
Written Opinion, dated Oct. 2, 2017, for corresponding International Patent Application PCT/IB2017/000921, 5 pages.
McClelland et al., "Complete genome sequence of *Salmonella enterica* serovar Typhimurium LT2." Nature. Oct. 23, 2001, vol. 413, pp. 852-856.
Bio-Rad Laboratories, Inc. User Guide for iQ-Check *Salmonella* II Kit. Catalog #: 357-8123. Code 808463. Revision G date: Feb. 2015; pp. 1-20.
ThermoFisher Scientific. User guide for TaqMan Assays for Food and Environmental Testing: Real-time PCR detection of pathogens in food and environmental samples. Publication No. MAN0009391, Revision C date: May 20, 2015; pp. 1-30.
Alvarez, et al. "Development of Multiplex PCR Technique for Detection and Epidemiological Typing of *Salmonella* in Human Clinical Samples." Journal of Clinical Microbiology, Apr. 2004, vol. 42, No. 4, p. 1734-1738.
Beaubrun et al. "The evaluation of a PCR-based method for identification of *Salmonella enterica* serotypes from environmental samples and various food matrices," Food Microbiology, 2012. vol. 31, pp. 199-209.
Hadjinicolaou et al. "Molecular beacon-based real-time PCR detection of primary isolates of *Salmonella typhimurium* and *Salmonella enteritidis* in environmental and clinical samples." BMC Microbiology, May 19, 2009, vol. 9, No. 97, pp. 1-14.
Lee et al. "A multiplex real-time PCR for differential detection and quantification of *Salmonella* ssp., *Salmonella enterica* serovar Typhimurium and Enteritidis in meats," Journal of Veterinary Science, 2009, vol. 10, No. 1, pp. 43-51.
McCarthy et al. "Sensitive and Rapid Molecular Detection Assays for *Salmonella enterica* Serovars Typhimurium and Heidelberg," Journal of Food Protection, Mar. 25, 2009. Vol. 72, No. 11, 2009, pp. 2350-2357.
Park et al. " Identification of *Salmonella enterica* subspecies I, *Salmonella enterica* serovars Typhimurium, Enteritidis and Typhi using multiplex PCR," FEEMS Microbiol lett, May 13, 2009, vol. 301, pp. 137-146.
Pui et al. "Multiplex PCR for the concurrent detection and differentiation of *Salmonella* spp., *Salmonella typhi* and *Salmonella typhimurium*," Tropical Medicine and Health, 2011. vol. 39, No. 1, pp. 9-15.
Shanmugasundaram et al. "Detection of *Salmonella enterica* serovar Typhimurium by selective amplification of fliC, fliB, iroB, invA, rfbJ, STM2755, STM4497 genes by polymerase chain reaction in a monoplex and multiplex format," World J Microbiol Biotechnol, Mar. 19, 2009, vol. 25, pp. 1385-1394.

(Continued)

*Primary Examiner* — Sarae L Bausch
(74) *Attorney, Agent, or Firm* — Kilpatrick Townsend & Stockton LLP

(57) ABSTRACT

Provided herein are methods and compositions for detecting *Salmonella* Typhimurium in a sample.

13 Claims, No Drawings

Specification includes a Sequence Listing.

(56) References Cited

OTHER PUBLICATIONS

Bioneer AccuPower® *Salmonella* Spp. 3-Plex PCR kit, downloaded on Apr. 9, 2019. Url: https://eng.bioneer.com/index.php/20-mas-1115.html.
Biotecon Diagnostics GmbH. User manual for foodproof® *Salmonella enteritidis* and Typhimurium Detection LyoKit—5'Nuclease—Version 2, Mar. 2017, pp. 1-9.
Anicon Labor GmBH directions for use for Kylt® SE/ST Triplex Real-Time PCR Detection Kit for detection of *Salmonella enteritidis* and *Salmonella typhimurium*. Publication No. FS.DNA-DK.SE/ST.02, Rev001, Dec. 2017. pp. 1-8.
English translation of Office Action dated Jan. 4, 2022 in CN Patent Application No. 201780037629.5. 17 pages.
Non-Final Office Action mailed Jun. 21, 2021 in U.S. Appl. No. 16/310,809, filed Jun. 15, 2017. 11 pages.
Sing, Pallavi et al.; "Massively parallel sequencing of enriched target amplicons for high-resolution genotyping of Salmonella serovars"; Molecular and Cellular Probes; 2013; vol. 27, No. 2; pp. 80-85.
Final Office Action mailed Dec. 8, 2021 in U.S. Appl. No. 16/310,809, filed Jun. 15, 2017. 19 pages.
Non-Final Office Action mailed Sep. 22, 2022 in U.S. Appl. No. 16/310,809, filed Jun. 15, 2017. 15 pages.
Liu, Bin et al.; "Development of a novel multiplex PCR assay for the identification of *Salmonella enterica* Typhimurium and Enteritidis"; Food Control; 2012; vol. 27, No. 1; pp. 87-93.
Final Office Action mailed Apr. 5, 2023 in U.S. Appl. No. 16/30,809, filed Jun. 15, 2017. 17 pages.
Notice of Allowance mailed Nov. 22, 2023 in U.S. Appl. No. 16/310,809, filed Jun. 15, 2017. 9 pages.

\* cited by examiner

SEQUENCE LISTING

```
Sequence total quantity: 9
SEQ ID NO: 1               moltype = DNA  length = 1388
FEATURE                    Location/Qualifiers
source                     1..1388
                           mol_type = unassigned DNA
                           organism = Salmonella enterica
                           note = Salmonella typhimurium
SEQUENCE: 1
atgtagctta agatatctat agtgatatca gtgtaatact tattggttag atcggtatga   60
tcttgaatat ttttatatcg atagtttgga ttacatagta gagttatttc actttgcaat   120
acagctttaa ttatagtttt gtcaagttgt aatttatcta taaaaatatt atttatagta   180
ttttctatta ggagaagtgt ttcgactaac ttgatatttg tattgatttt ttgtttgtag   240
atattccgta gcaattgagt tgaattgtgt tcaagcaatg gtgaacaaac ataatcccat   300
gattgctctt gagagtccca gtcattttta gctatttcaa tagcattggt gactaattcg   360
ataatttcat cttcaatttc tggatatggt actgaggcta attcaccact agtaaagcta   420
agtgtggggg ctagtattga taaataatgg tttacaaccg gagtgcacat taatcccgca   480
gcgtaaagca actcattttt gttatttgaa aagccgcaac ggcctgtatc atcaaaaaca   540
aaccctttg gacgatatct cacgcaaaaa ttaccttggc ttattttga ccatgttatg     600
ccttctctaa agtaatactc atcatttctt acggcagagc gagttttgcc attctcaaat   660
ttaaaatttc gtatttcgta accattattt tcccaattta caactatttc gttattacca   720
taccactttc gatattcacc tccactacta caaggaaacc atttgatatt atgaatgtcg   780
attttttgtat ttgattcttt atttgtgata agggtttttt ttattgaaac ctcgtaccaa  840
tatctttgaa atttaatatt gtcaccggtg gacatgcctg cttttaatgc tattttttct   900
ccaagttttt tatggtggcg aaaagataat agactcggta agtctatcca atatgctatt   960
ggcattcctg gtatgttttt aaaatcatgc tgtgtaaatt tatcaaatat attttttcctt  1020
agaagtagat cgcttttctt tacttcttcc ctaccatcta taagtctaaa aaatacaggt   1080
tggtaacgtt cggagtgttg gtttttaatc acccaggcag ttgtctgtac aacctctcca   1140
gaaatttgcc caaaagcccg agctcccaaa tgtgccatcg taataaatgt tttattgtcc   1200
aataaccagt tacgtagtgc ttcataactt gacaaaaaca tccatgattg catattgact   1260
tgagcattaa acccattttc tttaagcaaa gaaaatgcat tctgcataaa cattgcaaac   1320
aaatcagctt tactatccgg gaagttattt ttggcaaact ctttcagctc actattcatt   1380
cccttgcc                                                            1388

SEQ ID NO: 2               moltype = DNA  length = 947
FEATURE                    Location/Qualifiers
source                     1..947
                           mol_type = unassigned DNA
                           organism = Salmonella enterica
                           note = Salmonella typhimurium
SEQUENCE: 2
atgtagctta agatatctat agtgatatca gtgtaatact tattggttag atcggtatga   60
tcttgaatat ttttatatcg atagtttgga ttacatagta gagttatttc actttgcaat   120
acagctttaa ttatagtttt gtcaagttgt aatttatcta taaaaatatt atttatagta   180
ttttctatta ggagaagtgt ttcgactaac ttgatatttg tattgatttt ttgtttgtag   240
atattccgta gcaattgagt tgaattgtgt tcaagcaatg gtgaacaaac ataatcccat   300
gattgctctt gagagtccca gtcattttta gctatttcaa tagcattggt gactaattcg   360
ataatttcat cttcaatttc tggatatggt actgaggcta attcaccact agtaaagcta   420
agtgtggggg ctagtattga taaataatgg tttacaaccg gagtgcacat taatcccgca   480
gcgtaaagca actcattttt gttatttgaa aagccgcaac ggcctgtatc atcaaaaaca   540
aaccctttg gacgatatct cacgcaaaaa ttaccttggc ttattttga ccatgttatg     600
ccttctctaa agtaatactc atcatttctt acggcagagc gagttttgcc attctcaaat   660
ttaaaatttc gtatttcgta accattattt tcccaattta caactatttc gttattacca   720
taccactttc gatattcacc tccactacta caaggaaacc atttgatatt atgaatgtcg   780
attttttgtat ttgattcttt atttgtgata agggtttttt ttattgaaac ctcgtaccaa  840
tatctttgaa atttaatatt gtcaccggtg gacatgcctg cttttaatgc tattttttct   900
ccaagttttt tatggtggcg aaaagataat agactcggta agtctat                 947

SEQ ID NO: 3               moltype = DNA  length = 123
FEATURE                    Location/Qualifiers
source                     1..123
                           mol_type = unassigned DNA
                           organism = Salmonella enterica
                           note = Salmonella typhimurium
SEQUENCE: 3
taggagaagt gtttcgacta acttgatatt tgtattgatt ttttgtttgt agatattccg   60
tagcaattga gttgaattgt gttcaagcaa tggtgaacaa acataatccc atgattgctc   120
ttg                                                                 123

SEQ ID NO: 4               moltype = DNA  length = 22
FEATURE                    Location/Qualifiers
misc_feature               1..22
                           note = synthetic forward primer
source                     1..22
                           mol_type = other DNA
                           organism = synthetic construct
SEQUENCE: 4
taggagaagt gtttcgacta ac                                            22
```

```
SEQ ID NO: 5          moltype = DNA  length = 22
FEATURE               Location/Qualifiers
misc_feature          1..22
                      note = synthetic reverse primer
source                1..22
                      mol_type = other DNA
                      organism = synthetic construct
SEQUENCE: 5
caagagcaat catgggatta tg                                                   22

SEQ ID NO: 6          moltype = DNA  length = 29
FEATURE               Location/Qualifiers
misc_feature          1..29
                      note = synthetic probe
source                1..29
                      mol_type = other DNA
                      organism = synthetic construct
SEQUENCE: 6
tttacaattg agttgaattg tgttcaagc                                            29

SEQ ID NO: 7          moltype = DNA  length = 30
FEATURE               Location/Qualifiers
misc_feature          1..30
                      note = synthetic probe
source                1..30
                      mol_type = other DNA
                      organism = synthetic construct
SEQUENCE: 7
aaaagaacac aattcaactc aattgctacg                                           30

SEQ ID NO: 8          moltype = DNA  length = 25
FEATURE               Location/Qualifiers
misc_feature          1..25
                      note = synthetic probe
source                1..25
                      mol_type = other DNA
                      organism = synthetic construct
SEQUENCE: 8
caattgagtt gaattgtgtt caagc                                                25

SEQ ID NO: 9          moltype = DNA  length = 26
FEATURE               Location/Qualifiers
misc_feature          1..26
                      note = synthetic probe
source                1..26
                      mol_type = other DNA
                      organism = synthetic construct
SEQUENCE: 9
gaacacaatt caactcaatt gctacg                                               26
```

METHOD OF DETECTING *SALMONELLA TYPHIMURIUM*

CROSS-REFERENCE TO RELATED APPLICATION

This application is a continuation of U.S. patent application Ser. No. 16/310,809, filed Dec. 17, 2018, which is a national phase application under 35 U.S.C. 371 claiming priority to PCT/IB2017/000921, filed Jun. 15, 2017, which claims the benefit of U.S. Application 62/351,130 filed on Jun. 16, 2016, the content of each of which is hereby incorporated by reference for all purposes.

SEQUENCE LISTING

The instant application contains a Sequence Listing which has been submitted electronically herewith and is hereby incorporated by reference in its entirety. The ASCII copy, created on Feb. 22, 2024, is named 1050901_SEQ_ST25.txt, and is 5,026 bytes in size.

BACKGROUND

*Salmonella* is a leading cause of foodborne illnesses worldwide, with poultry and pork products being a primary source of infection to humans. Detecting *Salmonella* can be challenging because low levels of the bacteria may not be recovered using traditional culturing techniques. The genus *Salmonella*, member of the Enterobacteriaceae family, comprises two species *Salmonella enterica* and *Salmonella bongori*. *Salmonella enterica* is further divided into six subspecies, of which *S. enterica* subsp. *enterica* is the most clinically significant, causing 99% of *Salmonella* infections. The subspecies are further sub-divided into more than 2,500 serovars defined by somatic and flagellar antigens. *Salmonella enterica* subsp. *enterica* serovar Typhimurium and *Salmonella enterica* subsp. *enterica* serovar Enteritidis are the most frequently reported serovars associated with human cases of *Salmonella* infection from foodborne outbreaks. In the EU, a regulation in force since 2003 governs the mandatory detection of *Salmonella*. In 2011, this regulation was supplemented with the mandatory testing for *S*. Enteritidis and *S*. Typhimurium. According to Commission Regulation (EU) No. 1086/2011, all fresh poultry must be examined for *S*. Enteritidis and *S*. Typhimurium contamination. In the United States, the Food and Drug Administration (FDA) has published the Final Rule "Prevention of *Salmonella* Enteritidis in Shell Eggs During Production, Storage, and Transportation" (74 FR 33030), which will introduce methods requiring egg producers to test for *S*. Enteritidis. For non-egg producers, the FDA also published the guidance document for testing of human foods for *salmonella*: "Guidance for Industry: Testing for *Salmonella* Species in Human Foods and Direct-Human-Contact Animal Foods".

Conventional microbiological methods for the detection and identification of *Salmonella* serovars are very time consuming. The current accepted method for isolation of *Salmonella* from food and environmental primary production samples takes up to 5 days according to the ISO 6579. The most widely-used method used to characterize *Salmonella* into its subspecies is the Kauffman-White serotyping system, based on the variability of the O, H and Vi antigens.

SUMMARY

Described herein are methods and compositions for detecting *Salmonella* Typhimurium.

In an embodiment, a method of selectively detecting the presence of *Salmonella* Typhimurium in a sample comprises (a) providing a reaction mixture comprising a suitable primer pair for amplification of residues 749 to 2136 (1388 bp), or a portion thereof, of *Salmonella* Typhimurium ACCESSION CP007235 (SEQ ID NO:1); (b) performing PCR amplification of the nucleic acids of the sample using the reaction mixture of step (a); and (c) selectively detecting the presence of *Salmonella* Typhimurium by detecting the amplified nucleic acids. In some embodiments, the step (b) is performed in partitions. In some embodiments, the detecting the presence of *Salmonella* Typhimurium comprises sequencing the amplified nucleic acids.

In some embodiments, the reaction mixture comprises a primer pair for amplification of a sequence 95%, 97% or 99% homologous to SEQ ID NO: 1 or a portion thereof. In certain embodiments, the reaction mixture comprises a primer pair for amplification of residues 749 to 1697 (947 bp), or portions thereof, of *Salmonella* Typhimurium ACCESSION CP007235 (SEQ ID NO: 2). In some embodiments, the reaction mixture comprises a primer pair for amplification of a sequence 95%, 97% or 99% homologous to SEQ ID NO:2 or a portion thereof. In certain embodiments, the reaction mixture comprises a primer pair for amplification of residues 755 to 1063 (309 bp), or portions thereof, of *Salmonella* Typhimurium ACCESSION CP007235 (SEQ ID NO: 3). In some embodiments, the reaction mixture comprises a primer pair for amplification of a sequence 95%, 97% or 99% homologous to SEQ ID NO:3 or a portion thereof.

In an embodiment, the primer pair for amplification of the nucleic acid region of SEQ ID NO: 3 comprises the polynucleotide sequences set forth in SEQ ID NO:4 and SEQ ID NO:5. In an embodiment, the reaction mixture further comprises a probe for the nucleic acid region to be detected. In some embodiments, the probe comprises a detectable label. In some embodiment, the probe comprises the polynucleotide sequences set forth in SEQ ID NO:6 and SEQ ID NO:7. In certain embodiments, the probe comprises the polynucleotide sequences set forth in SEQ ID NO:6, SEQ ID NO:7, SEQ ID NO:8, or SEQ ID NO:9.

In an embodiment, an isolated polynucleotide comprises a polynucleotide sequence having at least 95% sequence identity based on the BLASTN method of alignment to the polynucleotide sequence set forth in SEQ ID NO:1. In some embodiments, the isolated polynucleotide sequence comprises a polynucleotide sequence set forth in SEQ ID NO:1. In an embodiment, an isolated polynucleotide comprises a polynucleotide sequence having at least 95% sequence identity based on the BLASTN method of alignment to the polynucleotide sequence set forth in SEQ ID NO:2. In some embodiments, the isolated polynucleotide sequence comprises a polynucleotide sequence set forth in SEQ ID NO:2. In an embodiment, an isolated polynucleotide comprises a polynucleotide sequence having at least 95% sequence identity based on the BLASTN method of alignment to the polynucleotide sequence set forth in SEQ ID NO:3. In some embodiments, the isolated polynucleotide sequence comprises a polynucleotide sequence set forth in SEQ ID NO:3.

In an embodiment, a kit for the detection of *Salmonella* Typhimurium in a sample comprises a primer pair comprising SEQ ID NO:4 and SEQ ID NO:5. In some embodiments, the kit further comprises a probe comprising SEQ ID NO:6 and SEQ ID NO:7. In some embodiments, the kit further comprises a probe comprising SEQ ID NO:6, SEQ ID NO: 7, SEQ ID NO:8, or SEQ ID NO:9. In certain embodiments, the kit further comprises at least one component selected from a lysis reagent, a DNA polymerase, at least one dNTP, a buffer, a negative control, a positive control, and instructions for performing a method to detect the presence of *Salmonella* Typhimurium in a nucleic acid sample.

DETAILED DESCRIPTION

Provided herein are methods of selectively detecting the presence of *Salmonella* Typhimurium in a sample. Also provided are compositions for use in the detection of *Salmonella* Typhimurium in a sample by nucleic acid amplification, e.g., by real-time PCR.

The disclosed detection method finds utility in the detection of *S.* Typhimurium in any type of sample, for example in samples for food testing, environmental testing, or human/animal diagnostic testing. Exemplary food samples include, but are not limited to, meats products, poultry (e.g., chicken, turkey), eggs, fish (e.g, cod), cookie dough, produce (e.g, lettuce, tomatoes), dairy (e.g. cheese, milk), milk powder (e.g., infant formula), chocolate (e.g., milk), cocoa, nacho cheese seasoning, pasta, pet food, peanut butter, soy flour, spices, and ready-to-eat food. Environmental samples include, but are not limited to, plastic, sealed concrete, and stainless steel. Other types of samples include, but are not limited to, water, stool, blood, urine, and tissue. Another type of sample includes weeds. The methods may be performed at the farm or processing facility prior to initial packaging, after packaging (e.g., prior to or after export from one country to another), or at the point of sale.

I. Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4$^{th}$ ed. 2007); Green et al., MOLECULAR CLONING, A LABORATORY MANUAL (FOURTH EDITION), Cold Spring Harbor Laboratory Press (Cold Spring Harbor, NY 2012).

The term "a" or "an" is intended to mean "one or more." The term "comprise" and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

The term "nucleic acid" refers to polymers of deoxyribonucleotides or ribonucleotides in either single- or double-stranded form, and complements thereof. The term "polynucleotide" refers to a linear sequence of nucleotides. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA.

"Polymerase chain reaction" is abbreviated PCR.

The term "isolated" refers to materials, such as nucleic acid molecules and/or proteins, which are substantially free or otherwise removed from components that normally accompany or interact with the materials in a naturally occurring environment. Isolated polynucleotides can be purified from a host cell in which they naturally occur. Conventional nucleic acid purification methods known to skilled artisans can be used to obtain isolated polynucleotides. The term also embraces recombinant polynucleotides and chemically synthesized polynucleotides.

The terms "polynucleotide", "polynucleotide sequence", "nucleic acid sequence", and "nucleic acid fragment" are used interchangeably herein. These terms encompass nucleotide sequences and the like. A polynucleotide can be a polymer of RNA or DNA that is single- or double-stranded, that optionally contains synthetic, non-natural, or altered nucleotide bases. A polynucleotide in the form of a polymer of DNA can be comprised of one or more strands of cDNA, genomic DNA, synthetic DNA, or mixtures thereof.

The term "amplification product" refers to nucleic acid fragments produced during a primer-directed amplification reaction. Typical methods of primer-directed amplification include polymerase chain reaction (PCR), ligase chain reaction (LCR), or strand displacement amplification (SDA). If PCR methodology is selected, the replication composition can comprise the components for nucleic acid replication, for example: nucleotide triphosphates, two (or more) primers with appropriate sequences, thermostable polymerase, buffers, solutes, and proteins.

The term "primer" refers to a synthetic oligonucleotide that is capable of acting as a point of initiation of nucleic acid synthesis or replication along a complementary strand when placed under conditions in which synthesis of a complementary strand is catalyzed by a polymerase. A primer can further contain a detectable label, for example a 5' end label.

The term "probe" refers to a synthetic oligonucleotide that is complementary (though not necessarily fully complementary) to a polynucleotide of interest and forms a duplexed structure by hybridization with at least one strand of the polynucleotide of interest. A probe can further contain a detectable label.

As used herein, the terms "label", "detectable label", and such refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, semiconductor nanocrystals, and ligands (e.g., biotin, avidin, streptavidin, or haptens). A detectable label can also include a combination of a reporter and a quencher.

The term "reporter" refers to a substance or a portion thereof which is capable of exhibiting a detectable signal, which signal can be suppressed by a quencher. The detectable signal of the reporter is, e.g., fluorescence in the detectable range; thus, a reporter can also be a label.

The term "quencher" refers to a substance which is capable of suppressing, reducing, inhibiting, etc., the detectable signal produced by the reporter.

As used herein, the term "quenching" refers to a process whereby, when a reporter and a quencher are in close proximity, and the reporter is excited by an energy source, a substantial portion of the energy of the excited state non-radiatively transfers to the quencher where it either dissipates nonradiatively or is emitted at a different emission wavelength than that of the reporter (e.g., by fluorescence resonance energy transfer or FRET).

The reporter can be selected from fluorescent organic dyes modified with a suitable linking group for attachment to the oligonucleotide, such as to the terminal 3' carbon or terminal 5' carbon. The quencher can also be selected from organic dyes, which may or may not be fluorescent, depending on the embodiment of the invention. Generally, whether the quencher is fluorescent or simply releases the transferred energy from the reporter by non-radiative decay, the absorption band of the quencher should at least substantially overlap the fluorescent emission band of the reporter to optimize the quenching.

Non-fluorescent quenchers or dark quenchers typically function by absorbing energy from excited reporters, but do not release the energy radiatively.

Selection of appropriate reporter-quencher pairs for particular probes can be undertaken in accordance with known techniques. Fluorescent and dark quenchers and their relevant optical properties from which exemplary reporter-quencher pairs can be selected are listed and described, for example, in R. W. Sabnis, HANDBOOK OF FLUORESCENT DYES AND PROBES, John Wiley and Sons, New Jersey, 2015, the content of which is incorporated herein by reference.

Reporter-quencher pairs can be selected from xanthene dyes including fluoresceins and rhodamine dyes. Many suitable forms of these compounds are available commercially with substituents on the phenyl groups, which can be used as the site for bonding or as the bonding functionality for attachment to an oligonucleotide. Another group of fluorescent compounds for use as reporters are the naphthylamines, having an amino group in the alpha or beta position. Included among such naphthylamino compounds are 1-dimethylaminonaphthy 1-5 sulfonate, 1-anilino-8-naphthalene sulfonate and 2-p-touidiny 1-6-naphthalene sulfonate. Other dyes include 3-phenyl-7-isocyanatocoumarin; acridines such as 9-isothiocyanatoacridine; N-(p-(2-benzoxazolyl)phenyl) maleimide; benzoxadiazoles; stilbenes; pyrenes and the like.

Suitable examples of quenchers can be selected from 6-carboxy-tetramethyl-rhodamine, 4-(4-dimethylaminophenylazo) benzoic acid (DABCYL™), tetramethylrhodamine (TAMRA™), BHQ-O™, BHQ-1™, BHQ-2™, and BHQ-3™, each of which are available from Biosearch Technologies, Inc. of Novato, Calif., Qy7™ QSY-9™, QSY-21™ and QSY-35™, each of which are available from Molecular Probes, Inc, Iowa Black™ FQ available from Integrated DNA Technologies.

Suitable examples of reporters can be selected from dyes such as SYBR green, 5-carboxyfluorescein (5-FAM™ available from Applied Biosystems of Foster City, Calif.), 6-carboxyfluorescein (6-FAM™), tetrachloro-6-carboxyfluorescein (TET), 2,7-dimethoxy-4,5-dichloro-6-carboxyfluorescein, hexachloro-6-carboxyfluorescein (HEX), 6-carboxy-2',4,7,7'-tetrachlorofluorescein (6-TET™ available from Applied Biosystems), carboxy-X-rhodamine (ROX™), 6-carboxy-4',5'-dichloro-2',7'-dimethoxyfluorescein (6-JOE™ available from Applied Biosystems), VIC™ dye products available from Molecular Probes, Inc., NED™ dye products available from Applied Biosystems, Cal Fluor dye products (such as, e.g., Cal Fluor Gold 540, Orange 560, Red 590, Red 610, Red 635) available from Biosearch Technologies, Quasar dye products (such as, e.g., Quasar 570, 670, 705) available from Biosearch Technologies, and the like.

The term "percent identity," in the context of two or more nucleic acids, refers to two or more sequences or subsequences that are the same or have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST™ or BLAST™ 2.0 sequence comparison algorithms with default parameters, or by manual alignment and visual inspection. See e.g., the NCBI web site at ncbi.nlm.nih.gov/BLAST. Such sequences are then said to be "substantially identical." Percent identity is typically determined over optimally aligned sequences, so that the definition applies to sequences that have deletions and/or additions, as well as those that have substitutions. The algorithms commonly used in the art account for gaps and the like. Typically, identity exists over a region comprising a sequence that is at least about 25 nucleotides in length, or over a region that is 50-100 nucleotides in length, or over the entire length of the reference sequence.

The terms "selectively" or "selective" with respect to nucleic acids refers to the discrimination between the target nucleic acid sequence (e.g., target sequence of *Salmonella* Typhimurium) over the non-target nucleic acid sequences (e.g., non-target sequence *Salmonella* Typhimurium). An assay is selective for a sequence if little or no hybridization of the primer or probe occurs with non-target sequence.

The terms "partitioning" or "partitioned" refer to separating an aqueous solution having one or more of a sample and reactant into a plurality of portions, or "partitions." Partitions can be solid or fluid. In some embodiments, a partition is a solid partition, e.g., a microchannel. In some embodiments, a partition is a fluid partition, e.g., a droplet. In some embodiments, a fluid partition (e.g., a droplet) is a mixture of immiscible fluids (e.g., water and oil). In some embodiments, a fluid partition (e.g., a droplet) is an aqueous droplet that is surrounded by an immiscible carrier fluid (e.g., oil).

II. Nucleic Acids

Genome Detection Regions

A detection method is provided herein that is based on the identification of residues 749 to 2136 (1388 bp) of *Salmonella* Typhimurium ACCESSION CP007235 (see SEQ ID NO: 1 in Table 1).

TABLE 1

Sequences

| SEQ ID NO | DESCRIPTION | SEQUENCE |
|---|---|---|
| 1 | 1388 bp fragment from the 3315 bp gene of *Salmonella* Typhimurium ACCESSION CP007235 | ATGTAGCTTAAGATATCTATAGTGATATCAGTGTAATACTTATTGGTTAG ATCGGTATGATCTTGAATATTTTTATATCGATAGTTTGGATTACATAGTA GAGTTATTTCACTTTGCAATACAGCTTTAATTATAGTTTTGTCAAGTTGT AATTTATCTATAAAAATATTATTTATAGTATTTTCTATTAGGAGAAGTGT TTCGACTAACTTGATATTTGTATTGATTTTTTGTTTGTAGATATTCCGTA GCAATTGAGTTGAATTGTGTTCAAGCAATGGTGAACAAACATAATCCCAT GATTGCTCTTGAGAGTCCCAGTCATTTTTAGCTATTTCAATAGCATTGGT |

TABLE 1-continued

Sequences

| SEQ ID NO | DESCRIPTION | SEQUENCE |
|---|---|---|
| | | GACTAATTCGATAATTTCATCTTCAATTTCTGGATATGGTACTGAGGCTA<br>ATTCACCACTAGTAAAGCTAAGTGTGGGGGCTAGTATTGATAAATAATGG<br>TTTACAACCGGAGTGCACATTAATCCCGCAGCGTAAAGCAACTCATTTTT<br>GTTATTTGAAAAGCCGCAACGGCCTGTATCATCAAAAACAAACCCTTTTG<br>GACGATATCTCACGCAAAAATTACCTTGGCTTATTTTTGACCATGTTATG<br>CCTTCTCTAAAGTAATACTCATCATTTCTTACGGCAGAGCGAGTTTTGCC<br>ATTCTCAAATTTAAAATTTCGTATTTCGTAACCATTATTTTCCCAATTTA<br>CAACTATTTCGTTATTACCATACCACTTTCGATATTCACCTCCACTACTA<br>CAAGGAAACCATTTGATATTATGAATGTCGATTTTTGTATTTGATTCTTT<br>ATTTGTGATAAGGGTTTTTTTATTGAAACCTCGTACCAATATCTTTGAA<br>ATTTAATATTGTCACCGGTGGACATGCCTGCTTTTAATGCTATTTTTTCT<br>CCAAGTTTTTTATGGTGGCGAAAAGATAATAGACTCGGTAAGTCTATCCA<br>ATATGCTATTGGCATTCCTGGTATGTTTTTAAAATCATGCTGTGTAAATT<br>TATCAAATATATTTTTCCTTAGAAGTAGATCGCTTTTCTTTACTTCTTCC<br>CTACCATCTATAAGTCTAAAAAATACAGGTTGGTAACGTTCGGAGTGTTG<br>GTTTTTAATCACCCAGGCAGTTGTCTGTACAACCTCTCCAGAAATTTGCC<br>CAAAAGCCCGAGCTCCCAATGTGCCATCGTAATAAATGTTTTATTGTCC<br>AATAACCAGTTACGTAGTGCTTCATAACTTGACAAAAACATCCATGATTG<br>CATATTGACTTGAGCATTAAACCCATTTTCTTTAAGCAAAGAAAATGCAT<br>TCTGCATAAACATTGCAAACAAATCAGCTTTACTATCCGGGAAGTTATTT<br>TTGGCAAACTCTTTCAGCTCACTATTCATTCCCTTGCC |
| 2 | 947 bp fragment of Salmonella Typhimurium ACCESSION CP007235 | ATGTAGCTTAAGATATCTATAGTGATATCAGTGTAATACTTATTGGTTAG<br>ATCGGTATGATCTTGAATATTTTTATATCGATAGTTTGGATTACATAGTA<br>GAGTTATTTCACTTTGCAATACAGCTTTAATTATAGTTTTGTCAAGTTGT<br>AATTTATCTATAAAAATATTATTTATAGTATTTTCTATTAGGAGAAGTGT<br>TTCGACTAACTTGATATTTGTATTGATTTTTTGTTTGTAGATATTCCGTA<br>GCAATTGAGTTGAATTGTGTTCAAGCAATGGTGAACAAACATAATCCCAT<br>GATTGCTCTTGAGAGTCCCAGTCATTTTTAGCTATTTCAATAGCATTGGT<br>GACTAATTCGATAATTTCATCTTCAATTTCTGGATATGGTACTGAGGCTA<br>ATTCACCACTAGTAAAGCTAAGTGTGGGGGCTAGTATTGATAAATAATGG<br>TTTACAACCGGAGTGCACATTAATCCCGCAGCGTAAAGCAACTCATTTTT<br>GTTATTTGAAAAGCCGCAACGGCCTGTATCATCAAAAACAAACCCTTTTG<br>GACGATATCTCACGCAAAAATTACCTTGGCTTATTTTTGACCATGTTATG<br>CCTTCTCTAAAGTAATACTCATCATTTCTTACGGCAGAGCGAGTTTTGCC<br>ATTCTCAAATTTAAAATTTCGTATTTCGTAACCATTATTTTCCCAATTTA<br>CAACTATTTCGTTATTACCATACCACTTTCGATATTCACCTCCACTACTA<br>CAAGGAAACCATTTGATATTATGAATGTCGATTTTTGTATTTGATTCTTT<br>ATTTGTGATAAGGGTTTTTTTATTGAAACCTCGTACCAATATCTTTGAA<br>ATTTAATATTGTCACCGGTGGACATGCCTGCTTTTAATGCTATTTTTTCT<br>CCAAGTTTTTTATGGTGGCGAAAAGATAATAGACTCGGTAAGTCTAT |
| 3 | 123 bp fragment of Salmonella Typhimurium ACCESSION CP007235 | TAGGAGAAGTGTTTCGACTAACTTGATATTTGTATTGATTTTTTGTTTGT<br>AGATATTCCGTAGCAATTGAGTTGAATTGTGTTCAAGCAATGGTGAACAA<br>ACATAATCCCATGATTGCTCTTG |
| 4 | Forward Primer for 123 bp target sequence spanning residues 937 to 958 | TAGGAGAAGTGTTTCGACTAAC |
| 5 | Reverse Primer for 123 bp target sequence spanning residues 1038 to 1059 | CAAGAGCAATCATGGGATTATG |
| 6 | Probe for 123 bp target sequence spanning residues 1000 to 1024 (5'FAM-3'BkFQ) | TTTACAATTGAGTTGAATTGTGTTCAAGC |
| 7 | Probe for 123 bp target sequence spanning residues 995 to 1020 (5'FAM™-3'BkFQ) | AAAAGAACACAATTCAACTCAATTGCTACG |

TABLE 1-continued

| Sequences | | |
|---|---|---|
| SEQ ID NO | DESCRIPTION | SEQUENCE |
| 8 | Probe for 123 bp target sequence spanning residues 1000 to 1024 (5'FAM™-3'BkFQ) | CAATTGAGTTGAATTGTGTTCAAGC |
| 9 | Probe for 123 bp target sequence spanning residues 995 to 1020 | GAACACAATTCAACTCAATTGCTACG |

Based on a publicly available software (e.g., BLAST™), SEQ ID NO: 1 is conserved (e.g., 100% sequence identity) in 672 *Salmonella* Typhimurium strains listed by Genbank accession number in Table 2.

TABLE 2

| Strains of *Salmonella Typhimurium* in which SEQ ID NO: 1 is 100% Conserved | | | |
|---|---|---|---|
| LVHC01000004.1 | LAPF01000001.1 | CTPI01000002.1 | CTHF01000003.1 |
| LVHA01000006.1 | LAPD01000063.1 | CTPH01000002.1 | CTHE01000002.1 |
| LVGZ01000004.1 | LAPC01000018.1 | CTPG01000002.1 | CTHD01000002.1 |
| LVGY01000004.1 | LAOX01000013.1 | CTPF01000002.1 | CTHC01000003.1 |
| LVGX01000005.1 | JZAH01000029.1 | CTPE01000003.1 | CTHB01000001.1 |
| LVGW01000004.1 | JZAB01000025.1 | CTPD01000001.1 | CTHA01000002.1 |
| LVGU01000047.1 | JYZR01000005.1 | CTPC01000003.1 | CTGZ01000002.1 |
| LVGT01000051.1 | JYZC01000010.1 | CTPB01000003.1 | CTGY01000002.1 |
| LVGS01000046.1 | JYZB01000030.1 | CTPA01000004.1 | CTGX01000005.1 |
| LVGR01000047.1 | JYYZ01000004.1 | CTOZ01000002.1 | CTGW01000025.1 |
| LVGQ01000013.1 | JYYU01000025.1 | CTOY01000002.1 | CTGV01000002.1 |
| LVGP01000004.1 | JYYT01000016.1 | CTOX01000003.1 | CTGU01000006.1 |
| LVGN01000006.1 | JYYQ01000066.1 | CTOW01000001.1 | CTGT01000002.1 |
| LVGM01000008.1 | JYYL01000011.1 | CTOV01000003.1 | CTGS01000002.1 |
| LVGL01000007.1 | JYYK01000018.1 | CTOU01000002.1 | CTGR01000004.1 |
| LVGK01000003.1 | JYYH01000035.1 | CTOT01000003.1 | CTGQ01000002.1 |
| LVGJ01000009.1 | JYYC01000006.1 | CTOS01000002.1 | CTGP01000004.1 |
| LVGI01000006.1 | JYYB01000003.1 | CTOR01000003.1 | CTGO01000001.1 |
| LVGH01000005.1 | JYYA01000024.1 | CTOQ01000004.1 | CTGN01000001.1 |
| LVGG01000006.1 | JYXZ01000019.1 | CTOP01000003.1 | CTGM01000002.1 |
| LVGF01000006.1 | JYXX01000004.1 | CTOO01000002.1 | CTGL01000004.2 |
| LVFW01000011.1 | JYXW01000003.1 | CTON01000002.1 | CTGK01000002.1 |
| LVFV01000011.1 | JYXT01000019.1 | CTOM01000004.1 | CTGJ01000035.1 |
| LVFT01000012.1 | JYXK01000009.1 | CTOL01000003.1 | CTGI01000004.1 |
| LVFS01000014.1 | JYXH01000002.1 | CTOK01000002.1 | CTGH01000004.1 |
| LVFR01000005.1 | JYXC01000008.1 | CTOJ01000001.1 | CTGG01000002.1 |
| LVFQ01000008.1 | JYWW01000034.1 | CTOI01000002.1 | CTGF01000002.1 |
| LVFP01000006.1 | JYWU01000014.1 | CTOH01000003.1 | CTGE01000002.1 |
| LVFO01000002.1 | JYWT01000009.1 | CTOG01000003.1 | CTGD01000002.1 |
| LVFN01000004.1 | JYWA01000003.1 | CTOF01000002.1 | CTGC01000002.1 |
| LVFM01000005.1 | JYVW01000007.1 | CTOE01000002.1 | CTGB01000004.1 |
| LVFL01000037.1 | JYVV01000004.1 | CTOD01000002.1 | CTGA01000002.1 |
| LVFK01000003.1 | JYVU01000035.1 | CTOC01000003.1 | CTFZ01000004.1 |
| LVFJ01000013.1 | JYVL01000001.1 | CTOB01000002.1 | CTFY01000002.1 |
| LVFI01000003.1 | JYVJ01000004.1 | CTOA01000004.1 | CTFX01000001.1 |
| LVFH01000010.1 | JYVG01000055.1 | CTNZ01000003.1 | CTFW01000003.1 |
| LUJG01000006.1 | JYVE01000037.1 | CTNY01000003.1 | CTFV01000004.1 |
| LUJF01000005.1 | JYUZ01000004.1 | CTNX01000002.1 | CTCJ01000002.1 |
| LUJE01000003.1 | JYUY01000010.1 | CTNW01000004.1 | CTCI01000003.1 |
| LUJC01000020.1 | JYUP01000020.1 | CTNV01000003.1 | CTGH01000003.1 |
| LUIZ01000005.1 | JYTX01000005.1 | CTNU01000002.1 | CTCG01000002.1 |
| LUIY01000005.1 | JYTW01000027.1 | CTNT01000002.1 | CTCF01000002.1 |
| LUIW01000007.1 | JYTU01000018.1 | CTNS01000003.2 | CTCE01000003.1 |
| LUIU01000061.1 | JYTT01000012.1 | CTNR01000001.1 | CTCD01000002.1 |
| UIT01000019.1 | JYTQ01000001.1 | CTNQ01000001.1 | CTCC01000044.1 |
| UIS01000029.1 | JYTP01000017.1 | CTNP01000002.1 | CTCB01000003.1 |
| LUIR01000027.1 | JYTL01000012.1 | CTNO01000002.1 | CTCA01000003.1 |
| LUIQ01000009.1 | JYTI01000010.1 | CTNN01000003.1 | CTBZ01000002.1 |
| LUIP01000019.1 | JYTD01000002.1 | CTNM01000002.1 | CTBY01000002.1 |
| LUIO001000023.1 | JYTB01000004.1 | CTNL01000002.1 | CTBX01000003.1 |

TABLE 2-continued

| Strains of *Salmonella Typhimurium* in which SEQ ID NO: 1 is 100% Conserved | | | |
|---|---|---|---|
| LUIN01000035.1 | JYSY01000001.1 | CTNK01000004.1 | CTBW01000004.1 |
| LUIM01000025.1 | JYSX01000031.1 | CTNJ01000001.1 | CTBV01000003.1 |
| LUIL01000040.1 | JYSO01000094.1 | CTNI01000002.1 | CTBU01000002.1 |
| LUIK01000041.1 | JYSN01000051.1 | CTNH01000002.1 | CTBT01000001.1 |
| LUIJ01000024.1 | JYSM01000007.1 | CTNG01000036.1 | CTBS01000003.1 |
| LUII01000036.1 | JYSL01000029.1 | CTNF01000003.1 | CTBR01000004.1 |
| LUIH01000014.1 | JYSG01000016.1 | CTNE01000002.1 | CTBQ01000003.1 |
| LUIG01000040.1 | JYSB01000024.1 | CTND01000002.1 | CTBP01000005.1 |
| LUIF01000036.1 | JYSA01000003.1 | CTNC01000001.1 | CTBO01000002.1 |
| LUIE01000017.1 | JYRX01000002.1 | CTNB01000046.1 | CTBN01000003.1 |
| LUID01000024.1 | JYRW01000014.1 | CTNA01000004.1 | CTBM01000003.1 |
| LUIC01000116.1 | JYRT01000085.1 | CTMZ01000002.1 | CTBK01000003.1 |
| LUIB01000040.1 | JYRQ01000034.1 | CTMY01000004.1 | CTBJ01000002.1 |
| LUIA01000027.1 | JYRM01000039.1 | CTMX01000002.1 | CTBI01000002.1 |
| LUHZ01000025.1 | JYRD01000017.1 | CTMW01000004.1 | CTBH01000003.1 |
| LUHY01000038.1 | JYRC01000016.1 | CTMV01000003.1 | CTBF01000004.1 |
| LUHX01000025.1 | JYQU01000020.1 | CTMU01000003.1 | CTBE01000004.1 |
| LUHV01000033.1 | JYQM01000015.1 | CTMT01000004.1 | CTBC01000002.1 |
| LUHU01000040.1 | JYQC01000008.1 | CTMS01000002.1 | CTBB01000002.1 |
| LUHT01000028.1 | JYQA01000030.1 | CTMR01000004.1 | CTBA01000002.1 |
| LUHS01000024.1 | JYPT01000005.1 | CTMQ01000003.1 | CTAZ01000003.1 |
| LUHR01000036.1 | JYPP01000050.1 | CTMP01000002.1 | CTAY01000001.1 |
| LONA01000003.1 | JYPO01000064.1 | CTMO01000003.1 | CTAX01000001.1 |
| LKJI01000024.1 | JYPM01000008.1 | CTMN01000003.1 | CTAW01000001.1 |
| LKJE01000032.1 | JUIT01000021.1 | CTMM01000003.1 | CTAV01000002.1 |
| LKJD01000006.1 | JRZW01000002.1 | CTML01000002.1 | CTAU01000001.1 |
| LJJK01000144.1 | JRZV01000001.1 | CTMK01000002.1 | CTAT01000003.1 |
| LIOJ01000001.1 | JRZU01000002.1 | CTMJ01000003.1 | CTAS01000002.1 |
| LIOG01000016.1 | JRZT01000030.1 | CTMI01000002.1 | CTAR01000002.1 |
| LIOF01000021.1 | JRZS01000015.1 | CTMH01000003.1 | CTAQ01000002.1 |
| LIOB01000013.1 | JRZR01000010.1 | CTMG01000002.1 | CTAP01000002.1 |
| LINM01000004.1 | JRZQ01000006.1 | CTMF01000002.1 | CTAO01000002.1 |
| LINL01000011.1 | JRZO01000062.1 | CTME01000001.1 | CTAN01000001.1 |
| LINK01000002.1 | JRZN01000054.1 | CTMD01000003.1 | CTAM01000004.1 |
| LINJ01000020.1 | JRZM01000003.1 | CTMC01000004.1 | CTAL01000003.1 |
| LINF01000009.1 | JRZL01000059.1 | CTMB01000002.1 | CTAK01000004.1 |
| LINE01000010.1 | JRZK01000010.1 | CTMA01000002.1 | CTAJ01000002.1 |
| LINB01000005.1 | SJRZJ01000012.1 | CTLZ01000002.1 | CTAI01000002.1 |
| LIMZ01000030.1 | SJRZI01000017.1 | CTLY01000002.1 | CTAH01000003.1 |
| LIMV01000008.1 | JRZH01000001.1 | CTLX01000004.1 | CTAG01000004.1 |
| LIMU01000022.1 | JRYU01000004.1 | CTLW01000002.1 | CTAF01000002.1 |
| LIMT01000027.1 | JRYT01000009.1 | CTLV01000004.1 | CTAE01000002.1 |
| LIMN01000012.1 | JRGW01000022.1 | CTLU01000001.1 | CTAD01000002.1 |
| LIMM01000010.1 | JRGV01000045.1 | CTLT01000004.1 | CTAC01000004.1 |
| LIMH01000001.1 | JRGU01000009.1 | CTLS01000004.1 | CTAB01000002.1 |
| LIDY01000003.1 | JRGT01000034.1 | CTLR01000003.1 | CQIE01000002.1 |
| LHOM01000023.1 | JRGS01000001.1 | CTLQ01000001.1 | CQHW01000002.1 |
| LHOJ01000006.1 | JRGR01000006.1 | CTLP01000003.1 | CQHV01000002.1 |
| LHOH01000004.1 | JHAI01000005.1 | CTLO01000001.1 | CQHU01000002.1 |
| LHOG01000003.1 | JHAH01000020.1 | CTLN01000003.1 | CQHS01000002.1 |
| LHOF01000033.1 | JHAG01000020.1 | CTLM01000004.1 | CQHR01000002.1 |
| LHNW01000001.1 | JHAF01000018.1 | CTLL01000004.1 | CQHQ01000002.1 |
| LHNS01000017.1 | JHAE01000013.1 | CTLK01000002.1 | CQHN01000002.1 |
| LHNM01000038.1 | FKJD01000009.1 | CTLJ01000002.1 | CQHJ01000001.1 |
| LHNL01000010.1 | FKJC01000004.1 | CTLI01000002.1 | CQHI01000002.1 |
| LHNI01000015.1 | FKJB01000003.1 | CTLH01000004.1 | CQHH01000002.1 |
| LHNH01000007.1 | CYID01000003.1 | CTLG01000004.1 | CQHG01000001.1 |
| LHNG01000002.1 | CYIC01000003.1 | CTLF01000002.1 | CQHF01000001.1 |
| LHMT01000026.1 | CYIB01000003.1 | CTLE01000002.1 | CQHE01000002.1 |
| LHMS01000025.1 | CYIA01000002.1 | CTLD01000004.1 | CQHD01000002.1 |
| LHMA01000007.1 | CYHZ01000003.1 | CTLC01000006.1 | CQHC01000002.1 |
| LHLX01000009.1 | CYHY01000003.1 | CTLB01000002.1 | CQHB01000002.1 |
| LHLU01000004.1 | CYHX01000003.1 | CTLA01000002.1 | CQHA01000001.1 |
| LHLP01000001.1 | CYHW01000002.1 | CTKZ01000002.1 | CQGZ01000001.1 |
| LHLO01000016.1 | CYHV01000002.1 | CTKI01000002.1 | CQGY01000002.1 |
| LHLK01000019.1 | CYHU01000003.1 | CTKG01000001.1 | CQGX01000002.1 |
| LHLF01000020.1 | CYHT01000003.1 | CTKD01000002.1 | CQGW01000002.1 |
| LHLA01000001.1 | CVMK01000002.1 | CTKC01000002.1 | CQGV01000002.1 |
| LHKL01000042.1 | CVMH01000002.1 | CTKB01000004.1 | CQGU01000002.1 |
| LHKK01000034.1 | CVKN01000003.1 | CTKA01000003.1 | CQGT01000001.1 |
| LHKD01000036.1 | CVKM01000005.1 | CTJZ01000002.1 | CQGS01000002.1 |
| LHKC01000003.1 | CVKK01000004.1 | CTJY01000002.1 | CQGR01000002.1 |
| LHKA01000038.1 | CVKJ01000005.1 | CTJX01000003.1 | CQGQ01000002.1 |
| LHJU01000003.1 | CVKH01000004.1 | CTJW01000002.1 | CQGP01000002.1 |
| LHJJ01000028.1 | CVKC01000002.1 | CTJV01000003.1 | CQGO01000002.1 |
| LHJF01000017.1 | CVKA01000004.1 | CTJU01000005.1 | CQGN01000002.1 |
| LHIX01000004.1 | CVJW01000001.1 | CTJT01000002.1 | CQGM01000002.1 |
| LHIW01000017.1 | CTQZ01000003.1 | CTJS01000002.1 | CQGL01000002.1 |

TABLE 2-continued

| Strains of *Salmonella Typhimurium* in which SEQ ID NO: 1 is 100% Conserved | | | |
|---|---|---|---|
| LHIR01000013.1 | CTQY01000002.1 | CTJR01000003.1 | CQGK01000001.1 |
| LHIQ01000047.1 | CTQX01000004.1 | CTJQ01000002.1 | CQGJ01000002.1 |
| LHIK01000014.1 | CTQU01000002.1 | CTJP01000002.1 | CQGI01000001.1 |
| LHIE01000015.1 | CTQT01000003.1 | CTJO01000004.2 | CQGH01000002.1 |
| LHID01000040.1 | CTQS01000002.1 | CTJN01000001.1 | CQGG01000002.1 |
| LHHK01000011.1 | CTQR01000002.1 | CTJM01000004.1 | CIJW01000002.1 |
| LHHB01000001.1 | CTQQ01000001.1 | CTJK01000003.1 | CIJD01000002.1 |
| LHGZ01000002.1 | CTQP01000002.1 | CTJJ01000002.1 | CHJY01000001.1 |
| LHGY01000001.1 | CTQO01000002.1 | CTIL01000002.1 | CGGH01000001.1 |
| LHGL01000047.1 | CTQN01000002.1 | CTIK01000003.1 | CGDA01000002.1 |
| LHGJ01000005.1 | CTQM01000002.1 | CTIJ01000003.1 | CGCS01000001.1 |
| LHGI01000006.1 | CTQL01000098.1 | CTII01000002.1 | CGCQ01000002.1 |
| LHGH01000003.1 | CTQK01000004.1 | CTIH01000002.1 | CGCH01000002.1 |
| LHFW01000031.1 | CTQJ01000002.1 | CTIG01000002.1 | CFOA01000002.1 |
| LHFV01000044.1 | CTQI01000001.1 | CTIF01000004.1 | CFNX01000002.1 |
| LHFU01000031.1 | CTQH01000001.1 | CTIE01000003.1 | CFLD01000002.1 |
| LHFT01000032.1 | CTQG01000002.1 | CTID01000002.1 | BAKU01000002.1 |
| LHFS01000022.1 | CTQF01000003.1 | CTIC01000002.1 | AYVJ01000114.1 |
| LHFP01000043.1 | CTQE01000004.1 | CTIB01000003.1 | AYUQ01000108.1 |
| LHFF01000013.1 | CTQD01000002.1 | CTIA01000004.1 | AUXR01000008.1 |
| LHEY01000021.1 | CTQC01000001.1 | CTHZ01000002.1 | AUXE01000003.1 |
| EHEX01000008.1 | CTQB01000003.1 | CTHY01000001.1 | AUVE01000003.1 |
| LHEW01000017.1 | CTQA01000002.1 | CTHX01000001.1 | AUVD01000043.1 |
| LHEV01000005.1 | CTPZ01000003.1 | CTHW01000001.1 | AUQU01000045.1 |
| LHER01000004.1 | CTPY01000003.1 | CTHV01000002.1 | AUQT01000034.1 |
| LHEQ01000025.1 | CTPX01000004.1 | CTHU01000002.1 | AUQO01000062.1 |
| LHEP01000049.1 | CTPW01000002.1 | CTHT01000004.1 | AUQN01000039.1 |
| LHEA01000005.1 | CTPV01000002.1 | CTHS01000002.1 | AUQM01000038.1 |
| LFGM01000013.1 | CTPU01000005.1 | CTHR01000002.1 | AOXO01000096.1 |
| LFDY01000028.1 | CTPT01000001.1 | CTHQ01000002.1 | AOXD01000065.1 |
| LFDW01000010.1 | CTPS01000002.1 | CTHP01000002.1 | AOXC01000083.1 |
| LFCC01000059.1 | CTPR01000003.1 | CTHO01000004.1 | AJTU01000007.1 |
| LDPA01000008.1 | CTPQ01000002.1 | CTHN01000002.1 | AHVA01000018.1 |
| LAPQ01000066.1 | CTPP01000002.1 | CTHM01000002.1 | AHUZ01000018.1 |
| LAPP01000078.1 | CTPO01000002.1 | CTHL01000002.1 | AHUV01000085.1 |
| LAPO01000058.1 | CTPN01000002.1 | CTHK01000002.1 | AHUT01000031.1 |
| LAPN01000091.1 | CTPM01000005.1 | CTHJ01000001.1 | AHUS01000047.1 |
| LAPM01000076.1 | CTPL01000004.1 | CTHI01000039.1 | AERV01000023.1 |
| LAPH01000042.1 | CTPK01000003.1 | CTHH01000002.1 | ABAO01000006.1 |
| LAPG01000091.1 | CTPJ01000002.1 | CTHG01000002.1 | LUIV01000062.1 |

Also based on a publicly available software (e.g., BLAST), SEQ ID NO: 1 is partially conserved (e.g., at least 99% sequence identity) in 48 *Salmonella* Typhimurium strains listed by Genbank accession number in Table 3.

TABLE 3

| Strains of *Salmonella Typhimurium* in which SEQ ID NO: 1 is Partially Conserved | | | |
|---|---|---|---|
| LVGO01000006.1 | LUJA01000002.1 | LDYH01000006.1 | AMEA02000013.1 |
| LVGE01000003.1 | LUIX01000003.1 | JYPX01000009.1 | AMDZ02000027.1 |
| LVGD01000004.1 | LFGR01000011.1 | JTED01000004.1 | AMDY01000216.1 |
| LVGC01000003.1 | LFGQ01000013.1 | AUQV01000023.1 | AMDX02000108.1 |
| LVGB01000001.1 | LFGP01000017.1 | ATWR01000084.1 | JRZX01000002.1 |
| LVGA01000003.1 | LFGN01000015.1 | AMEH02000182.1 | JRZP01000003.1 |
| LVFZ01000005.1 | LFDX01000009.1 | AMEG02000055.1 | AUQL01000040.1 |
| LVFY01000001.1 | LFCI01000010.1 | AMEF02000044.1 | LFGO01000009.1 |
| LVFX01000003.1 | LFCH01000028.1 | AMEE02000031.1 | LFDZ01000012.1 |
| LVFU01000005.1 | LFCG01000008.1 | AMED02000059.1 | LECA01000009.1 |
| LUJD01000002.1 | LECD01000013.1 | AMEC02000055.1 | LUHW01000058.1 |
| LUJB01000005.1 | LECC01000010.1 | AMEB02000105.1 | LECB01000012.1 |

Based on a publicly available software (e.g., BLAST), SEQ ID NO: 1 is not found in the following non-Typhimurium *Salmonella* strains:

*Salmonella_enterica*_serovar_Ohio_CFSAN001079
*Salmonella_enterica*_serovar_Newport_WA14881
*Salmonella enterica*_serovar_Schwarzengrund_SL480
*Salmonella_enterica*_serovar_Gallinarum 28791
*Salmonella_enterica*_serovar_Thompson_2010K1863
*Salmonella_enterica*_serovar_Kentucky_CDC191
*Salmonella_enterica*_serovar_Typhi BL196
*Salmonella_enterica*_serovar Enteritidis P125109
*Salmonella_enterica*_serovar_Agona_72A52
*Salmonella_enterica*_serovar_Saintpaul_JO2008
*Salmonella_enterica*_serovar_Heidelberg_SL476
*Salmonella_enterica*_serovar_Virchow_ATCC51955
*Salmonella_enterica*_serovar_Paratyphi_B_SARA62
*Salmonella_enterica* serovar MontevideoMDA09249507
*Salmonella_enterica*_serovar Muenchen 2009K0951
*Salmonella_enterica*_serovar_Bareilly_CFSAN000197
*Salmonella_enterica*_serovar_Virchow_SL491

*Salmonella_enterica*_serovar_Pullorum_19945
*Salmonella_enterica*_serovar_Dublin_SL1438
*Salmonella_enterica*_serovar_Stanley_060538

In another embodiment, a detection method is based on the identification of residues 749-1697 of *Salmonella* Typhimurium ACCESSION CP007235 REGION: 658819 . . . 662133 (see SEQ ID NO:2 in Table 1). In another embodiment, a detection method is based on the identification of residues 755-1063 of *Salmonella* Typhimurium ACCESSION CP007235 REGION: 658819 . . . 662133 (see SEQ ID NO:3 in Table 1). In some embodiments, the detection method incorporates unlabeled primers and labeled probes for the detection of *Salmonella* Typhimurium.

Oligonucleotides

Oligonucleotides of the instant invention are set forth in SEQ ID NOs: 4-9.

Disclosed oligonucleotides can be used as primers for PCR amplification and as hybridization probes. Primers and probes are shown in Table 1.

The nucleic acid probes can contain a detectable label. In some embodiments, the probe comprises a reporter-quencher combination as employed in a double-stranded probe, a TAQMAN™ probe, a molecular beacon probe, a SCORPION™ probe, a dual hybridization probe, or an ECLIPSE™ probe. In some embodiments, a double-stranded probe comprises two completely or partially complementary strands. In some embodiments, one strand of the double-stranded probe comprises a reporter on the 5' end and the other strand comprises a quencher on the 3' end such that when the two strands hybridize, the reporter and quencher face each other and the quencher quenches the fluorescence emitted by the reporter. During PCR, the strands separate, allowing the reporter to fluoresce and to be detected. In some embodiments, each strand of the double-stranded probe includes a reporter at one end (e.g., the 5' end) and a quencher at the other end (e.g., the 3' end). When the two strands hybridize with each other, the reporter from the first strand is in close proximity with the quencher of the second strand such that fluorescence quenching occurs. During PCR, the strands separate, allowing the reporter to fluoresce and to be detected. In an embodiment, the probe is a double-stranded probe as described in U.S. Pat. No. 9,194,007, which is incorporated by reference in its entirety herein. In an embodiment, a reporter-quencher pair used in a double-stranded probe is 6-FAM™ and Iowa Black® FQ.

III. Methods

The oligonucleotides can be used in a method for selectively detecting the presence of *Salmonella* Typhimurium in a sample. In an embodiment, the method begins by providing a reaction mixture comprising a suitable primer pair for amplification of residues 749-1697, or a portion thereof, of SEQ ID NO:2. In some embodiments, the reaction mixture comprises a primer pair for amplification of a sequence 95%, 97%, or 99% homologous to SEQ ID NO:2. In some embodiments, the reaction mixture comprises a primer pair for amplification of a sequence of SEQ ID NO:2 or a portion thereof.

In certain embodiments, the reaction mixture comprises a primer pair for amplification of residues 755-1063, or portions thereof, of SEQ ID NO:3. In some embodiments, the reaction mixture comprises a primer pair for amplification of a sequence 95%, 97%, or 99% homologous to SEQ ID NO:3. In some embodiments, the reaction mixture comprises a primer pair for amplification of a sequence of SEQ ID NO:3 or a portion thereof. In some embodiments, the primer pair for amplification of the nucleic acid region of SEQ ID NO:3 comprises SEQ ID NO: 4 and SEQ ID NO:5.

In some embodiments, the method further comprises a probe for the nucleic acid region to be detected. In certain embodiments, the probe comprises a detectable label. In some embodiments, the probe is a single-stranded probe comprising SEQ ID NO:6, SEQ ID NO:7, SEQ ID NO:8, or SEQ ID NO:9. In some embodiments, each probe is labeled with a reporter on one end (e.g., the 5' end) and a quencher on the other end (e.g., the 3' end). In some embodiments, the probe is a double-stranded probe comprising SEQ ID NO:6 and SEQ ID NO:7 (e.g., SEQ ID NO:6 can hybridize to SEQ ID NO:7) with each strand having a reporter on one end (e.g., the 5' end) and a quencher on the other end (e.g., the 3' end).

The next step of the method comprises performing PCR amplification (e.g., real-time PCR) of the nucleic acids of the sample using the reaction mixture. In some embodiments, PCR amplification is performed in partitions (e.g, droplets). Methods and compositions for partitioning a solution are described, for example, in published patent applications WO 2012/135259, WO 2014/117088, WO 2010/036352, and U.S. Pat. No. 9,156,010, the entire content of each of which is incorporated by reference herein.

In the last step of the method, the presence of *Salmonella* Typhimurium is selectively detected by detecting the amplified nucleic acids. In some embodiments, the detecting step comprises sequencing the amplified nucleic acids.

IV. Kits

In another aspect, kits for detecting *Salmonella* Typhimurium in a sample according to the methods described herein are provided. In some embodiments, a kit comprises a primer pair as described herein. In some embodiments, the kit further comprises probes as described herein. In some embodiments, the kit further comprises assay components including, but not limited to, a lysis reagent, a DNA polymerase, dNTPs, a buffer, a negative control, and a positive control. In some embodiments, the kit further comprises instructions for carrying out the methods described herein.

V. Examples

Example 1—Comparison of *Salmonella* Typhimurium Assay of the Instant Invention to *Salmonella* Spp. Assay In this example, the *Salmonella* Typhimurium assay of the instant invention was compared to a commercially available *Salmonella* spp. Assay. In the experiment, eleven *Salmonella* serovars that are most relevant for the food industry were tested with the *Salmonella* Typhimurium assay of this disclosure and with the iQ-Check™ *Salmonella* spp. II Assay (Bio-Rad). The eleven *Salmonella* strains were streaked on a TCS Petri dish and allowed to grow for 24 hr at 37° C. Individual colonies were then picked, diluted in 500 µL sterile water and 5 µL were tested with each assay using the Bio-Rad CFX96 Touch™ Real-Time PCR Detection System. For the *Salmonella* Typhimurium assay, the double-stranded probe comprised SEQ ID NOs 6 and 7. Each strand of the double-stranded probe was labeled with 6-FAM™ on the 5' end and Iowa Black™ FQ on the 3' end. The double-stranded probe was synthesized by Integrated DNA Technologies using phosphoramidite chemistry. Results are shown in Table 4.

TABLE 4

Comparison of Assays

| | Bio-Rad iQ-Check *Salmonella* spp. II assay | | | *Salmonella Typhimurium* assay | | |
|---|---|---|---|---|---|---|
| Serovars | Target Cq | Internal control Cq | Result | Target Cq | Internal control Cq | Result |
| Negative ctrl | N/A | 32.84 | Negative | N/A | 32.49 | Negative |
| Positive ctrl | 31.72 | 32.24 | Positive | 31.95 | 31.78 | Positive |
| Typhimurium | 19.69 | 34.60 | Positive | 19.36 | 33.43 | Positive |
| Monophasic Typhimurium | 18.35 | N/A | Positive | 18.08 | 34.2 | Positive |
| Enteritidis | 20.34 | 32.72 | Positive | N/A | 32.15 | Negative |
| Infantis | 20.86 | 32.40 | Positive | N/A | 31.78 | Negative |
| Virchow | 19.71 | 33.28 | Positive | N/A | 32 | Negative |
| Hadar | 21,20 | 32.29 | Positive | N/A | 31.89 | Negative |
| Paratyphi B Java | 20.24 | 33.27 | Positive | N/A | 31.91 | Negative |
| Livingstone | 20.84 | 33.21 | Positive | N/A | 32.38 | Negative |
| Kentucky | 18.67 | 34.26 | Positive | N/A | 32.17 | Negative |
| Dublin | 21,24 | 32.68 | Positive | N/A | 31.99 | Negative |
| Newport | 20.23 | 32.67 | Positive | N/A | 31.98 | Negative |

The results shown in Table 4 illustrate that only typhimurium is detected by the *Salmonella* Typhimurium assay. The results also show that the sensitivities of both assays are identical and that the *Salmonella* Typhimurium assay can be used as a primary screening assay or as a confirmatory, serotyping assay.

Example 2—Assay Selectivity

This example illustrates assay selectivity of the instant invention. One-hundred and nine *Salmonella enterica* subsp. *enterica* serovars and *Salmonella enterica* subspecies (in italics in Table 4) were tested with the *Salmonella* Typhimurium assay. The same method and probes as in Example 1 were used in this experiment. The organisms tested are shown in Table 5.

TABLE 5

| Selectivity |
|---|
| Abaetetuba |
| Aberdeen |
| Adelaïde |
| Agama |
| Albany |
| Anatum |
| *arizonae* |
| Bambylor |
| Bareilly |
| Berta |
| Betioky |
| Blegdam |
| Blockley |
| *bongori* |
| Braenderup |
| Brandenburg |
| Bredeney |
| Budapest |
| California |
| Cerro |
| Carrau |
| Canoga |
| Crossness |
| Cubana |
| *Choleraesuis* |
| *diarizonae** |
| Dalhem |
| Derby |
| Dublin |
| Emek |
| Duisberg |

TABLE 5-continued

| Selectivity |
|---|
| Enteritidis |
| Fischerkietz |
| Ferruch |
| Give |
| Gaminara |
| Gallinarum |
| Glostrup |
| Grumpensis |
| Grabow |
| Goldgoast |
| Havana |
| Hadar |
| Guinea |
| Havanna |
| *houtenae** |
| Illinois |
| Heidelberg |
| Indiana |
| *indica** |
| Inverness |
| Johannesburg |
| Infantis |
| Kentucky |
| Kirkee |
| Kottbus |
| Kedougou |
| Lomita |
| Livingstone |
| Manica |
| London |
| Miami |
| Minnesota |
| Maregrosso |
| Mbandaka |
| Muenchen |
| Montevideo |
| Moscow |
| Napoli |
| Nienstedten |
| Naestved |
| Newport |
| Nottingham |
| Oranienburg |
| Ouakam |
| Okatie |
| Ohio |
| Phoenix |
| Panama |
| Paratyphi B** |
| Paratyphi B java |
| Postdam |
| Poona |

TABLE 5-continued

Selectivity

Puttin
Quentin
Rostock
Salamae
Rubislaw
Senftenberg
Saint Paul
Schwarzengrund
Singapore
Sheffield
Sundsvall
Springs
Strasbourg
Taksony
Tallahassee
Tournai
Tenessee
Thompson
Treforest
Tranoroa
Utrecht
Virchow
Zuerich
Yoruba
Wayne
Worthington Of the organisms listed in Table 5, all but Paratyphi B were not detected with the assay. The results illustrate that the *Salmonella* Typhimurium assay is highly selective for *Salmonella* Typhimurium.

Example 3—Assay Exclusivity

This example illustrates assay exclusivity of the instant invention. Thirty-nine non-*Salmonella* bacteria were tested with the *Salmonella* Typhimurium assay. The same method and probe as in Example 1 was used in this experiment. The bacteria tested are tabulated in Table 6. None of the bacteria listed in Table 6 were detected by the *Salmonella* Typhimurium assay, illustrating assay exclusivity.

TABLE 6

Exclusivity

*Acinetobacter baumanii*
*Aeromonas hydrophila*
*Aeromonas hydrophila/caviae*
*Bacillus licheniformis*
*Bacillus cereus*
*Campylobacter jejuni*
*Campylobacter coli*
*Campylobacter lari*
*Campylobacter upsaliensis*
*Citrobacter freundii*
*Cronobacter sakazakii*
*Enterobacter cloacae*
*Enterobacter pyrinus*
*Enterobacter sakazakii*
*Enterobacter aerogenes*
*Enterobacter asburiae*
*Enterobacter amnigenus*
*Enterobacter cowanii*
*Enterococcus faecium*
*Escherichia coli*
*Escherichia hermanii*
*Hafnia alvei*
*Klebsiella oxytoca*
*Klebsiella pneumoniae*
*Listeria monocytogenes*
*Micrococcus luteus*
*Pantoea agglomerans*
*Proteus mirabilis*
*Pseudomonas fluorescens*
*Pseudomonas aeruginosa*
*Raoultella terrigena*
*Serratia marcescens*
*Shigella flexneri*
*Shigella sonnei*
*Staphylococcus aureus*
*Staphylococcus internmedius*
*Staphylococcus xylosus*
*Staphylococcus epidermidis*
*Yersinia enterocoloitica*

Example 4—Assay Specificity

This example illustrates assay specificity of the instant invention. Seventy-nine *Salmonella* Typhimurium serovars were tested with the *Salmonella* Typhimurium assay. The same method and probe as in Example 1 was used in this experiment. The bacteria tested are tabulated in Table 7. All of the bacteria listed in Table 7 were detected by the *Salmonella* Typhimurium assay, illustrating assay specificity.

TABLE 7

Specificity

| Serovar | Antigenic formula | Comment | Primary source | Origin | Strain number (Bio-Rad Library) | Strain number (Other Library) |
|---|---|---|---|---|---|---|
| *Typhimurium* | 1,4,[5],12:i:1,2 | | Anses | Brine | 002 | no Anses: 38.09 |
| *Typhimurium* | 1,4,[5],12:i:1,2 | | Anses | Beef meat | 003 | no Anses: 442.09 |
| *Typhimurium* | 1,4,[5],12:i:1,2 | | Anses | Pork (crépine de porc) | 004 | no Anses: 447.09 |
| *Typhimurium* | 1,4,[5],12:i:1,2 | | Anses | Lamb with sauce | 005 | no Anses: 591.09 |
| *Typhimurium* | 1,4,[5],12:i:1,2 | | Anses | Stuffed quail | 006 | no Anses: 695.09 |
| *Typhimurium* | 1,4,[5],12:i:1,2 | | Anses | Culture from lamb feces | 007 | no Anses: 839.09 |
| *Typhimurium* | 1,4,[5],12:i:1,2 | | Anses | Environment (Duck) | 008 | no Anses: 838.09 |
| *Typhimurium* | 1,4,[5],12:i:1,2 | | Anses | Culture from horse feces | 009 | no Anses: 553.11 |
| *Typhimurium* | 1,4,[5],12:i:1,2 | | Anses | White pepper | 010 | no Anses: 564.11 |
| *Typhimurium* | 1,4,[5],12:i:1,2 | | Anses | Hoki filet with cream | 011 | no Anses: 708.11 |
| *Typhimurium* | 1,4,[5],12:i:1,2 | | Anses | Pigeon viscera | 012 | no Anses: 781.11 |

TABLE 7-continued

| | | | | | | Strain number | Strain number |
|---|---|---|---|---|---|---|---|
| Serovar | Antigenic formula | Comment | Primary source | Origin | | (Bio-Rad Library) | (Other Library) |
| Typhimurium | 1,4,[5],12:i:1,2 | | Anses | Compost | | 013 | no Anses: 792.11 |
| Typhimurium | 1,4,[5],12:i:1,2 | | Anses | Environmental (Chicken) | | 014 | no Anses: 835.11 |
| Typhimurium | 1,4,[5],12:i:1,2 | | Anses | Streaky ham | | 015 | no Anses: 840.11 |
| Typhimurium | 1,4,[5],12:i:1,2 | | Anses | Whole quail | | 016 | no Anses: 845.11 |
| Typhimurium | 1,4,[5],12:i:1,2 | | Anses | Spareribs | | 017 | no Anses: 880.11 |
| Typhimurium | 1,4,[5],12:i:1,2 | | Anses | Culture from swine feces | | 018 | no Anses: 886.11 |
| Typhimurium | 1,4,[5],12:i:1,2 | | Anses | Raw milk (cow) | | 019 | no Anses: 907.11 |
| Typhimurium | 1,4,[5],12:i:1,2 | | Anses | Sausage | | 020 | no Anses: 976.11 |
| Typhimurium | 1,4,[5],12:i:1,2 | | Anses | Tomato filling | | 021 | no Anses: 977.11 |
| Typhimurium | 1,4,[5],12:i:1,2 | | Anses | Stuffed potatoes | | 022 | no Anses: 979.11 |
| Typhimurium | 1,4,[5],12:i:1,2 | | Anses | Fish meal | | 023 | no Anses: 985.11 |
| Typhimurium | 1,4,[5],12:i:1,2 | | Anses | Pet food | | 043 | no Anses: 1175.11 |
| Typhimurium | 1,4,[5],12:i:1,2 | | Anses | Foie gras (Liver) | | 030 | no Anses: 119.11 |
| Typhimurium | 1,4,[5],12:i:1,2 | | ADRIA Development | Milk powder | | 081 | ADRIA no4 |
| Typhimurium | 1,4,[5],12:i:1,2 | | ADRIA Development | Pasteurized liquid egg | | 082 | ADRIA no13 |
| Typhimurium | 1,4,[5],12:i:1,2 | | ADRIA Development | Pasteurized liquid egg | | 083 | ADRIA no206 |
| Typhimurium | 1,4,[5],12:i:1,2 | | ADRIA Development | Egg yolk | | 084 | ADRIA no472 |
| Typhimurium | 1,4,[5],12:i:1,2 | | ADRIA Development | Pasteurized liquid egg | | 085 | ADRIA no776 |
| Typhimurium | 1,4,[5],12:i:1,2 | | ADRIA Development | Ready-to-eat | | 086 | CIP 58.58 |
| Typhimurium | 1,4,[5],12:i:1,2 | | ADRIA Development | Foie (Liver) | | 087 | ADRIA no19 |
| Typhimurium | 1,4,[5],12:i:1,2 | | ADRIA Development | Raw ground meat | | 088 | ADRIA no22 |
| Typhimurium | 1,4,[5],12:i:1,2 | | ADRIA Development | Ready-to-eat | | 089 | ADRIA no167 |
| Typhimurium | 1,4,[5],12:i:1,2 | | ADRIA Development | Chipolatas sausages | | 090 | ADRIA no193 |
| Typhimurium | 1,4,[5],12:i:1,2 | | ADRIA Development | Chipolatas sausages | | 091 | ADRIA no830 |
| Typhimurium | 1,4,[5],12:i:1,2 | | ADRIA Development | Merguez sausages | | 092 | ADRIA no911 |
| Typhimurium | 1,4,[5],12:i:1,2 | | ADRIA Development | Chipolatas sausages | | 093 | ADRIA no987 |
| Typhimurium | 1,4,[5],12:i:1,2 | | ADRIA Development | Meat (pâté) | | 094 | ADRIA no4874 |
| Typhimurium | 1,4,[5],12:i:1,2 | | ADRIA Development | Frozen meat | | 095 | A00C003 |
| Typhimurium | 1,4,[5],12:i:1,2 | | ADRIA Development | Frozen meat | | 096 | A00C004 |
| Typhimurium | 1,4,[5],12:i:1,2 | | ADRIA Development | Frozen beef trim | | 097 | A00C059 |
| Typhimurium | 1,4,[5],12:i:1,2 | | ADRIA Development | ground beef | | 098 | A00C060 |
| Typhimurium | 1,4,[5],12:i:1,2 | | ADRIA Development | Pork | | 106 | Ad1070 |
| Typhimurium | 1,4,[5],12:i:1,2 | | ADRIA Development | Pork | | 107 | ST325 |
| Typhimurium | 1,4,[5],12:i:1,2 | | ADRIA Development | Pork | | 108 | ST1 |
| Typhimurium | 1,4,[5],12:i:1,2 | | ADRIA Development | Pork | | 109 | ST394 |
| Typhimurium | 1,4,[5],12:i:1,2 | | ADRIA Development | Pork | | 110 | ST719 |
| Typhimurium | 1,4,[5],12:i:1,2 | | ADRIA Development | Pork | | 111 | ST11 |
| Typhimurium | 1,4,[5],12:i:1,2 | | ADRIA Development | Liquid egg | | 113 | JES411 |
| Typhimurium | 1,4,[5],12:i:1,2 | | ADRIA Development | Beef trim | | 116 | Ad913 |

TABLE 7-continued

| Serovar | Antigenic formula | Comment | Primary source | Origin | Strain number (Bio-Rad Library) | Strain number (Other Library) |
|---|---|---|---|---|---|---|
| Typhimurium | 1,4,[5],12:i:1,2 | | ADRIA Development | Pork | 118 | Ad1249 |
| Typhimurium | 1,4,[5],12:i:1,2 | | ADRIA Development | pork (crépine) | 119 | Ad1338 |
| Typhimurium | 1,4,[5],12:i:1,2 | | ADRIA Development | ground meat | 120 | Ad1410 |
| Typhimurium | 1,4,[5],12:i:1,2 | | ADRIA Development | Liquid egg | 121 | Ad1484 |
| Typhimurium | 1,4,[5],12:i:1,2 | | ADRIA Development | Drinking water from trough | 122 | Ad1546 |
| Typhimurium | 1,4,[5],12:i:1,2 | | ADRIA Development | salmon with vegetables | 123 | Ad1603 |
| Typhimurium | 1,4,[5],12:—:— | non motile variant | ADRIA Development | Tiramisu | 124 | Ad1333 |
| Typhimurium | 1,4,[5],12:—:1,2 | monophasic variant | ADRIA Development | Hen | 125 | Ad1335 |
| Typhimurium | 1,4,[5],12:i:— | monophasic variant | ADRIA Development | Pork specialty | 126 | Ad1334 |
| Typhimurium | 1,4,[5],12:i:1,2 | | Anses | Environmental (Quail) | 160 | 2002LSAL00347 |
| Typhimurium | 1,4,[5],12:i:1,2 | | Anses | Environmental (goose) | 161 | 2016LSAL02607 |
| Typhimurium | 1,4,[5],12:i:— | monophasic variant | Anses | Environmental (Pork) | 162 | 2009LSAL04410 |
| Typhimurium | 1,4,[5],12:—:1,2 | monophasic variant | Anses | Environmental (Gallus gallus-hen) | 163 | 2010LSAL01759 |
| Typhimurium | 1,4,[5],12:i:— | monophasic variant | Anses | Environmental | 164 | 2011LSAL04681 |
| Typhimurium | 1,4,[5],12:i:— | monophasic variant | Anses | Environmental (Turkey) | 165 | 2012LSAL04635 |
| Typhimurium | 1,4,[5],12:i:1,2 | | Anses | Environmental (Gallus gallus) | 166 | 2013LSAL00987 |
| Typhimurium | 1,4,[5],12:i:— | monophasic variant | Anses | Environmental (Bovine) | 167 | 2014LSAL00857 |
| Typhimurium | 1,4,[5],12:i:— | monophasic variant | Anses | Pork meat | 168 | 2011LSAL06561 |
| Typhimurium | 1,4,[5],12:i:— | monophasic variant | Anses | Veal meat | 169 | 2012LSAL05317 |
| Typhimurium | 1,4,[5],12:i:— | monophasic variant | Anses | Turkey meat | 170 | 2014LSAL02635 |
| Typhimurium | 1,4,[5],12:i:— | monophasic variant | Anses | Gallus gallus meat | 171 | 2014LSAL03913 |
| Typhimurium | 1,4,[5],12:i:— | monophasic variant | Anses | Poultry Feed | 172 | 2011LSAL04983 |
| Typhimurium | 1,4,[5],12:i:— | monophasic variant | Anses | cattle feed | 173 | 2012LSAL03407 |
| Typhimurium | 1,4,[5],12:i:— | monophasic variant | Anses | animal blood products | 174 | 2012LSAL03874 |
| Typhimurium | 1,4,[5],12:i:— | monophasic variant | Anses | cattle feed | 175 | 2015LSAL00792 |
| Typhimurium | 1,4,[5],12:i:— | monophasic variant | Anses | beef meat (carcass) | 176 | 2013LSAL02030 |
| Typhimurium | 1,4,[5],12:i:— | monophasic variant | Anses | pork (carcass) | 177 | 2015LSAL01461 |
| Typhimurium | 1,4,[5],12:i:— | monophasic variant | Anses | turkey (carcass) | 178 | 2013LSAL03886 |
| Typhimurium | 1,4,[5],12:i:— | monophasic variant | Anses | chicken (carcass) | 179 | 2016LSAL00194 |

It is understood that the examples and embodiments described herein are for illustrative purposes only and that various modifications or changes in light thereof will be suggested to persons skilled in the art and are to be included within the spirit and purview of this application and scope of the appended claims. All patents, patent applications, internet sources, and other published reference materials cited in this specification are incorporated herein by reference in their entireties. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A probe comprising a polynucleotide comprising SEQ ID NO:6 or SEQ ID NO:7.

2. The probe of claim 1, comprising SEQ ID NO:6 and SEQ ID NO:7.

3. The probe of claim 1, wherein the probe comprises a detectable label.

4. A kit for the detection of *Salmonella* Typhimurium in a sample, the kit comprising:
   a primer pair comprising a first primer comprising SEQ ID NO:4 and a second primer comprising SEQ ID NO:5 and
   a probe comprising SEQ ID NO:6 or SEQ ID NO:7.

5. The kit of claim 4, wherein the probe comprises SEQ ID NO:6 and SEQ ID NO:7.

6. The kit of claim 4, further comprising a probe comprising SEQ ID NO:8, or SEQ ID NO:9.

7. The kit of claim 4, further comprising at least one component selected from a lysis reagent, a DNA polymerase, dNTPs, a buffer, a negative control, a positive control, and instructions for performing a method to detect the presence of *Salmonella* Typhimurium in a nucleic acid sample.

8. The kit of claim 4, wherein the probe comprises a detectable label.

9. The kit of claim 8, wherein the detectable label is selected from the group consisting of a radioactive isotope, fluorescer, chemiluminescer, enzyme, chromophore, dye, metal ion, metal sol, semiconductor nanocrystal, dark quencher and fluorescence quencher.

10. The probe of claim 1, wherein the probe is a double-stranded probe wherein the polynucleotide comprising SEQ ID NO:6 hybridizes to the polynucleotide comprising SEQ ID NO:7 and wherein each strand of the probe comprises a reporter on a first strand end and a quencher on a second strand end.

11. The probe of claim 3, wherein the detectable label is selected from the group consisting of a radioactive isotope, fluorescer, chemiluminescer, enzyme, chromophore, dye, metal ion, metal sol, semiconductor nanocrystal, dark quencher and fluorescence quencher.

12. The probe of claim 1, wherein the polynucleotide comprises SEQ ID NO:6.

13. The probe of claim 1, wherein the polynucleotide comprises SEQ ID NO:7.

* * * * *